United States Patent
Lyon et al.

(10) Patent No.: US 6,803,196 B1
(45) Date of Patent: Oct. 12, 2004

(54) METHODS AND COMPOSITIONS FOR DETECTING SIGNALS IN BINDING ASSAYS USING MICROPARTICLES

(75) Inventors: William A. Lyon, San Jose, CA (US); Huu Minh Tran, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/687,932

(22) Filed: Oct. 13, 2000

(51) Int. Cl.[7] .............................. C12Q 1/68; C12N 9/00; C12M 1/34; C07K 16/00; C07H 21/02
(52) U.S. Cl. ..................... 435/6; 435/91.1; 435/91.2; 435/183; 435/287.2; 436/501; 436/507; 436/532; 436/94; 436/172; 436/800; 436/809; 536/23.1; 536/24.3; 530/387.1; 530/391.1; 530/810
(58) Field of Search .................... 435/6, 91.1, 91.2, 435/287.2, 183; 436/94, 501, 507, 532, 538, 172, 800, 809; 536/23.1, 24.3, 24.31, 24.33; 530/387.1, 391.1, 810

(56) References Cited

U.S. PATENT DOCUMENTS

| | | |
|---|---|---|
| 4,882,269 A | 11/1989 | Schneider et al. |
| 5,132,242 A | 7/1992 | Cheung et al. |
| 5,194,300 A | 3/1993 | Cheung et al. |
| 5,561,043 A | 10/1996 | Cantor et al. |
| 5,571,670 A | 11/1996 | Urdea et al. |
| 5,573,909 A | 11/1996 | Singer et al. |
| 5,614,362 A | 3/1997 | Urdea et al. |
| 5,747,255 A * | 5/1998 | Brenner .................... 435/6 |
| 5,989,813 A | 11/1999 | Gerdes et al. |
| 6,027,897 A | 2/2000 | Lorincz et al. |
| 6,103,474 A | 8/2000 | Dellinger et al. |
| 6,110,687 A | 8/2000 | Nilsen |
| 6,117,631 A | 9/2000 | Nilsen |
| 6,136,535 A | 10/2000 | Lorincz et al. |
| 6,203,989 B1 * | 3/2001 | Goldberg et al. .............. 435/6 |
| 6,221,581 B1 | 4/2001 | Engelhardt et al. |
| 6,245,513 B1 | 6/2001 | Lane et al. |
| 6,261,779 B1 | 7/2001 | Barbera-Guillem et al. |
| 6,319,670 B1 | 11/2001 | Sigal et al. |
| 6,355,431 B1 | 3/2002 | Chee et al. |

FOREIGN PATENT DOCUMENTS

| | | | |
|---|---|---|---|
| EP | 0 999 285 A1 | | 5/2000 |
| EP | 0999285 A1 | * | 5/2000 |

* cited by examiner

Primary Examiner—Bradley L. Sisson
(74) Attorney, Agent, or Firm—Sandra E. Wells; Philip L. McGarrigle

(57) ABSTRACT

Methods and compounds are provided for detecting target molecules in a sample using specific binding assays. In particular, methods are provided for detecting a nucleic acid target in a sample. In one embodiment, the presently claimed invention provides a method of labeling a hybridized target wherein the target comprises a binding ligand. In another embodiment, the presently claimed invention provides methods of signal amplification.

9 Claims, 5 Drawing Sheets

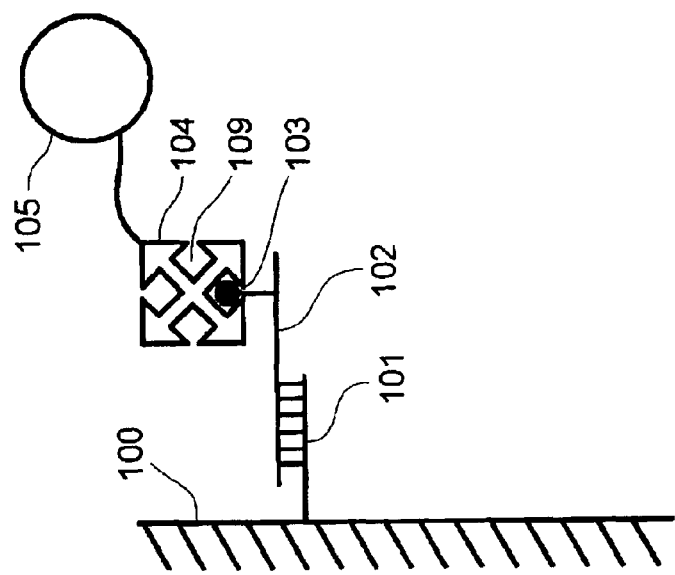
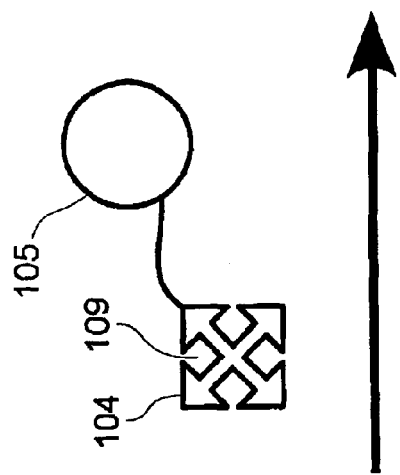
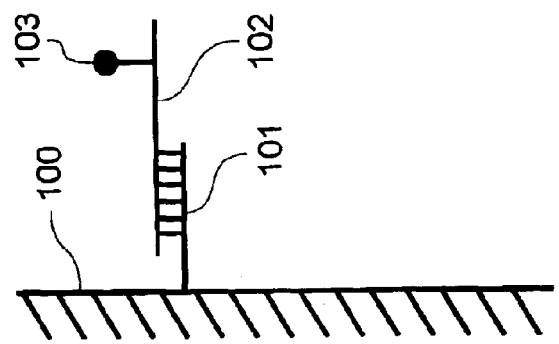
Fig. 1

METHODS AND COMPOSITIONS FOR DETECTING SIGNALS IN BINDING ASSAYS USING MICROPARTICLES

This invention relates generally to methods and compounds for the detection of polymers and for amplifying detectable signals in specific binding assays, particularly nucleic acid hybridization assays. Nucleic acid hybridizations are commonly used in biochemical research and diagnostic assays. Generally a single stranded analyte nucleic acid is hybridized to labeled nucleic acid probe, and resulting nucleic acid duplexes are detected. Radioactive and nonradioactive labels have been used. Methods also have been developed to amplify the signal that is detected.

Methods for the detection of nucleic acid sequences have suffered from drawbacks including background noise, time and labor requirements, lack of specificity and lack of sensitivity. It is an object of the invention to provide materials for the detection of polymers, particularly nucleic acids. It is a particular object of the invention to provide methods for labeling nucleic acid sequences in specific binding assays. It is a further object of the invention to provide methods and compounds for amplifying signals used in the detection of nucleic acid sequences in specific binding assays. It is an even further object of the invention to provide methods and compounds that permit nucleic acid sequences to be detected specifically and rapidly with high sensitivity and high resolution.

SUMMARY OF THE INVENTION

Methods and compounds are provided for detecting target molecules using specific binding assays. Methods and compositions are provided that are useful in signal amplification in the detection of target molecules.

In one embodiment, methods are provided for detecting a target molecule, wherein the method comprises hybridizing a target to an immobilized probe, wherein the target comprises a binding ligand. The hybridized target is contacted with a receptor that is capable of binding the binding ligand. Attached to the receptor is a detectable microparticle. The presence of the complexed microparticle is then detected.

Optionally, the presently claimed invention provides methods for amplifying the detectable signal. The method comprises hybridizing a target molecule to a probe wherein the target comprises a binding ligand. The hybridized target is contacted with a first receptor comprising multiple sites capable of binding the binding ligand to complex the receptor to the binding ligand, the first receptor may or may not be attached to a detectable moiety. The first receptor is contacted with a microparticle that is conjugated to a plurality of anti-receptors that themselves comprise a binding ligand. The microparticle may or may not be detectable. The anti-receptors are exposed to a second receptor that is conjugated to a detectable moiety. The first and second receptor may or may not be the same.

In one preferred embodiment, the probe is immobilized on a surface. The surface may be, for example, Langmuir Blodgett film, glass, germanium, silicon, (poly) tetrafluorethylene, polystyrene, gallium arsenide, gallium phosphide, silicon oxide, silicon nitride, and combinations thereof.

In a further embodiment, a method for detecting a nucleic acid target is provided, wherein the method includes providing a surface comprising at least 100 nucleic acid probes each in an area of less than about 0.1 cm$^2$, and each nucleic acid probe having a defined sequence and location on the surface, and contacting the surface with a nucleic acid target to permit the nucleic acid target to hybridize with at least one selected nucleic acid probe, wherein the target comprises a binding ligand. The method further includes contacting the hybridized target with a receptor that is conjugated to a detectable microparticle. Alternatively, the method comprises contacting the hybridized target with a receptor comprising a plurality of binding sites which may or may not be conjugated to a detectable moiety; contacting the receptor with an anti-receptor comprising multiple binding ligands wherein the anti-receptor is conjugated to a microparticle which may or may not be detectable; and exposing the above complex to a plurality of second receptors which are themselves complexed to detectable moieties.

Also provided are complexes including a nucleic acid comprising a binding ligand; a receptor; and microparticle.

In another embodiment, there is provided a substrate comprising a surface having immobilized thereon a nucleic acid probe, comprising a probe nucleic acid sequence, hybridized to a nucleic acid target, comprising a target nucleic acid sequence; wherein the target comprises a binding ligand, and wherein the binding ligand on the target is complexed with a receptor comprising multiple sites capable of binding the binding ligand, and wherein the receptor is complexed to a detectable microparticle.

In a further embodiment, there is provided a substrate comprising a surface having immobilized thereon a nucleic acid probe hybridized to a nucleic acid target; wherein the target comprises a binding ligand, and wherein the binding ligand on the target is complexed with a first receptor comprising a plurality of binding sites which may or may not be conjugated to a detectable moiety; the first receptor being complexed to an anti-receptor comprising multiple binding ligands wherein the anti-receptor is conjugated to a microparticle which may or may not be detectable; and the multiple binding ligands on the anti-receptor being complexed to a plurality of second receptors which are themselves complexed to detectable moieties.

BRIEF DESCRIPTION OF THE DRAWINGS

FIG. 1 is a schematic illustration of one embodiment of the presently claimed invention in which a hybridized target molecule comprising a binding ligand is complexed to a receptor comprising a detectable microparticle.

DETAILED DESCRIPTION OF THE PREFERRED EMBODIMENTS

1. Definitions

Figure 2:
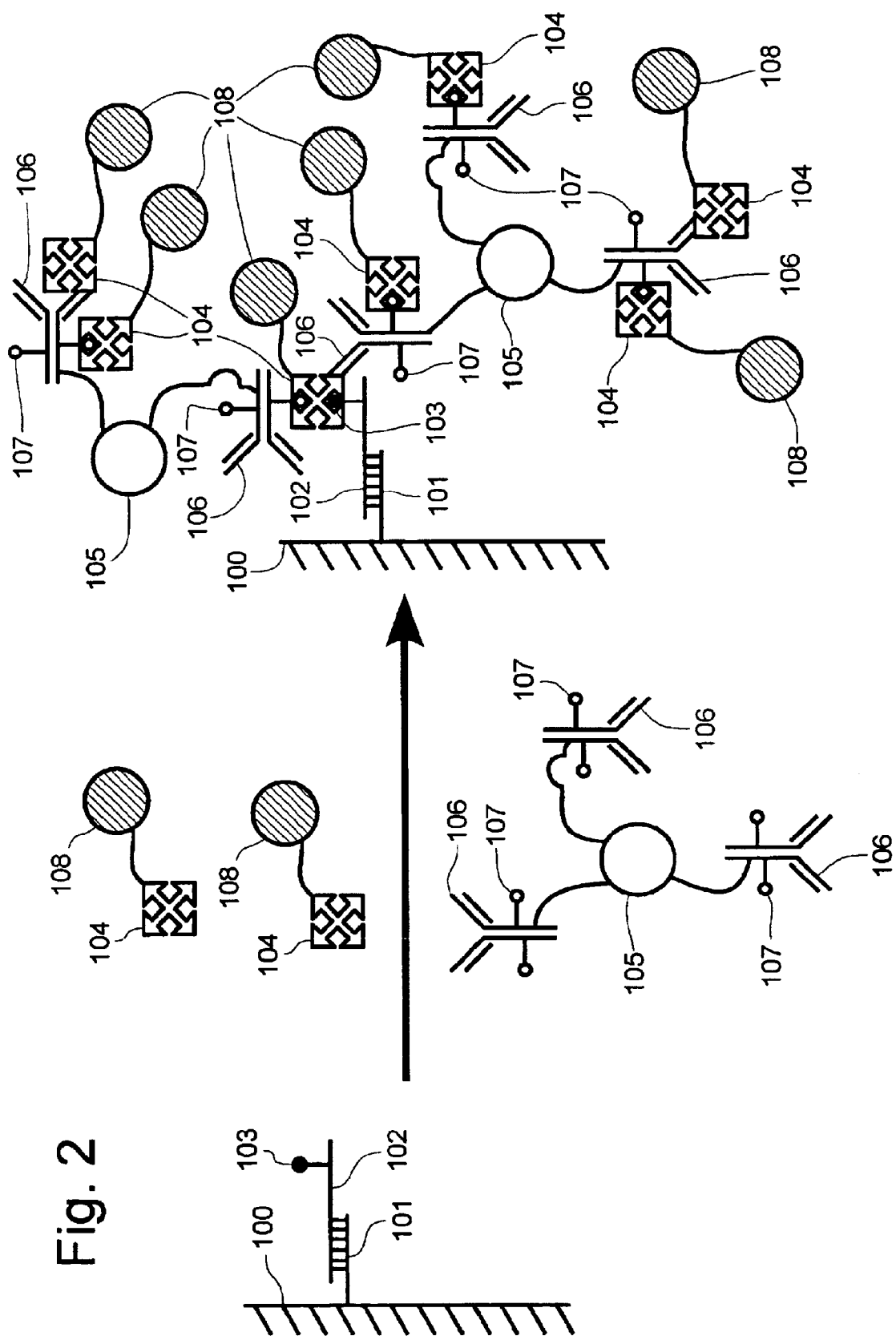
FIG. 2 is a schematic illustration of one embodiment of the presently claimed invention in which signal amplification is achieved by complexing a hybridized target molecule to a plurality of detectable moieties via a detectable microparticle.

As used herein, the term "antibody" refers to an immunoglobulin molecule or a fragment of an immunoglobulin molecule having the ability to specifically bind to a particular antigen. Generally, an antibody contains the ligand to bind the receptor. The antibody may be an anti-receptor antibody specific for the receptor used in the assay. Thus, the antibody may be capable of specifically binding the receptor as the antigen. Antibodies and methods for their manufacture are well known in the art of immunology. The antibody may be produced, for example, by hybridoma cell lines, by immunization to elicit a polyclonal antibody response, or by recombinant host cells that have been transformed with a recombinant DNA expression vector that encodes the antibody. Antibodies include but are not limited to immunoglobulin molecules of any isotype (IgA, IgG, IgE, IgD, IgM), and active fragments including Fab, Fab', F(ab')$_2$, Facb, Fv, ScFv, Fd, $V_H$ and $V_L$. Antibodies include but are not limited to single chain antibodies, chimeric antibodies, mutants, fusion proteins, humanized antibodies and any other modified configuration of an immunoglobulin molecule that comprises an antigen recognition site of the required specificity.

As used herein, "hybridization" refers to the binding association between two nucleic acids, for example the non-covalent interaction via base pair hydrogen bonding and base stacking. The ability of two single stranded nucleic acids to hybridize will depend upon factors such as their degree of complementarity as well as the stringency of the hybridization reaction conditions.

As used herein, the phrase "ligand-receptor pair" refers to a ligand and receptor that are chemical moieties capable of recognizing and binding to each other. The ligand and receptor can be any moieties that are capable of recognizing and binding to each other to form a complex. Additionally, the ligand and receptor may interact via the binding of a third intermediary substance. Typically, the ligand and receptor constituting the ligand-receptor pair are binding molecules that undergo a specific noncovalent binding interaction with each other. The ligand and receptor can be naturally occurring or artificially produced, and optionally may be aggregated with other species. An antibody may be one part of a ligand-receptor pair.

As used herein a "microparticle" refers to a polymer sphere with a surface containing chemically reactive functional groups for attaching ligands, receptors, or labels. The microparticle may have a diameter of between 1 nm and 10 um and more preferably has a diameter of between 10 nm and 500 mn.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. A polynucleotide may comprise modified nucleotides, such as methylated nucleotides and nucleotide analogs. A polynucleotide may comprise peptide nucleic acids (PNAs). The sequence of nucleotides may be interrupted by non-nucleotide components.

As used herein, "stringency" refers to the conditions of a hybridization reaction that influence the degree to which nucleic acids hybridize. Stringent conditions can be selected that allow nucleic acid duplexes to be distinguished based on their degree of mismatch. High stringency is correlated with a lower probability for the formation of a duplex containing mismatched bases. Thus, the higher the stringency, the greater the probability that two single-stranded nucleic acids, capable of forming a mismatched duplex, will remain single-stranded. Conversely, at lower stringency, the probability of formation of a mismatched duplex is increased. The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art. See, for example, Sambrook, et al., "Molecular Cloning: A Laboratory Manual," Second Edition, Cold Spring Harbor Laboratory Press, 1989; Ausubel, et al., "Current Protocols In Molecular Biology," John Wiley & Sons, 1987, 1988, 1989, 1990, 1991, 1992, 1993, 1994, 1995, 1996 and periodic updates; and Hames et al., "Nucleic Acid Hybridization: A Practical Approach," IRL Press, Ltd., 1985. In general, conditions that increase stringency (i.e., select for the formation of more closely-matched duplexes) include higher temperature, lower ionic strength and presence or absence of solvents; lower stringency is favored by lower temperature, higher ionic strength, and lower or higher concentrations of solvents (for example, lower concentrations of formamide or dimethyl sulfoxide). The duration of the hybridization reaction and the concentration of reactants (i.e., single stranded nucleic acid) can also affect stringency, with short reaction times and low reactant concentrations favoring higher stringency.

A variety of patents, patent applications and publications are cited throughout the specification. Unless otherwise specified, each of these patents, patent applications and publications is incorporated by reference in its entirety for all purposes.

2. General

Methods and compounds are provided for detecting target molecules using specific binding assays. In particular, methods are provided for detecting a nucleic acid target.

In one embodiment, the presently claimed invention provides methods for detectably labeling a hybridized target molecule. The method comprises hybridizing a target molecule to a probe wherein the target comprises a binding ligand. The hybridized target is contacted with a receptor comprising multiple sites capable of binding the binding ligand to complex the receptor to the binding ligand, the receptor being complexed to a detectable microparticle. The presence of the complexed receptor then is detected, for example, by detecting the presence of the detectable microparticle. A schematic illustration of this embodiment is depicted in FIG. 1.

In FIG. 1 a probe 101 is affixed to a solid support 100. A target molecule 102 containing a first binding ligand 103 is hybridized to the immobilized probe 101. A detectable microparticle 105 that is conjugated to multiple first receptors 104 is introduced. Each first receptor 104 comprises multiple first binding sites 109 that are capable of binding the first binding ligand 103, thus producing a complex capable of being detected comprising a solid support 100 to which a probe 101 is immobilized that is hybridized to a target molecule 102 comprising a first binding ligand 103. The first binding ligand 103 is complexed to a first receptor 104 comprising a detectable moiety 105.

As a non-limiting example of the above embodiment, a DNA probe of known sequence may be immobilized to a glass substrate at a known location. A plurality of biotinylated nucleic acid sequences are exposed to the DNA probe. A nucleic acid target sequence comprising a portion that is complementary to the DNA probe is allowed to hybridize to the DNA probe. Non-hybridized sequences are removed. A fluorescein-dyed microparticle conjugated to streptavidin is introduced. The streptavidin complexes to the biotin on the target sequence. Any non-complexed microparticles are removed. The presence of the target is determined by optically detecting the presence of the fluorescent microparticle.

Optionally, the microparticle may comprise a plurality of binding ligands to which detectable anti-ligands may be attached. This permits the detectable signal to be enhanced and more easily detected.

Figure 3:
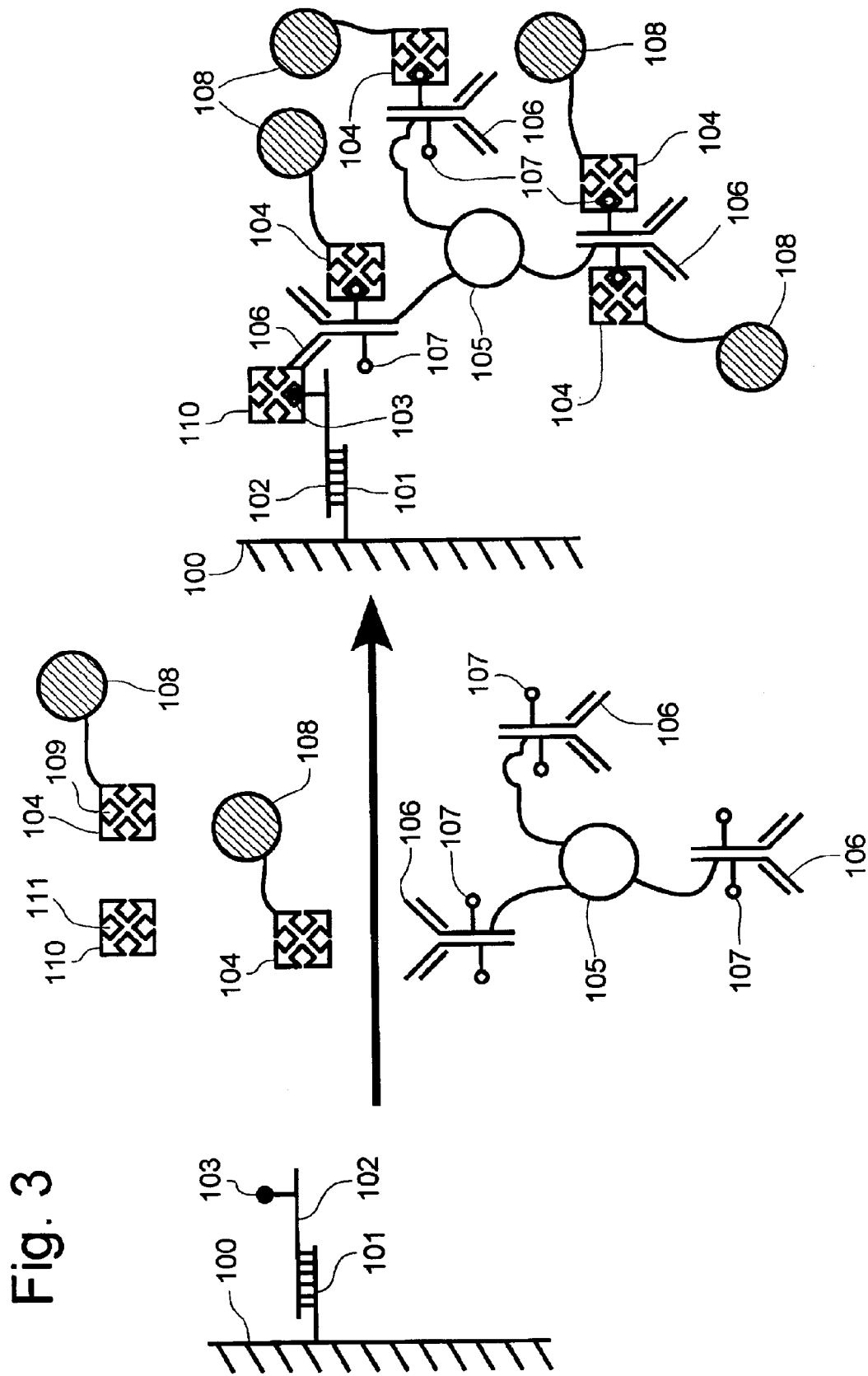
FIG. 3 is a schematic illustration of one embodiment of the presently claimed invention in which signal amplification is achieved by complexing a hybridized target molecule to a plurality of detectable moieties via a microparticle.
Figure 4:
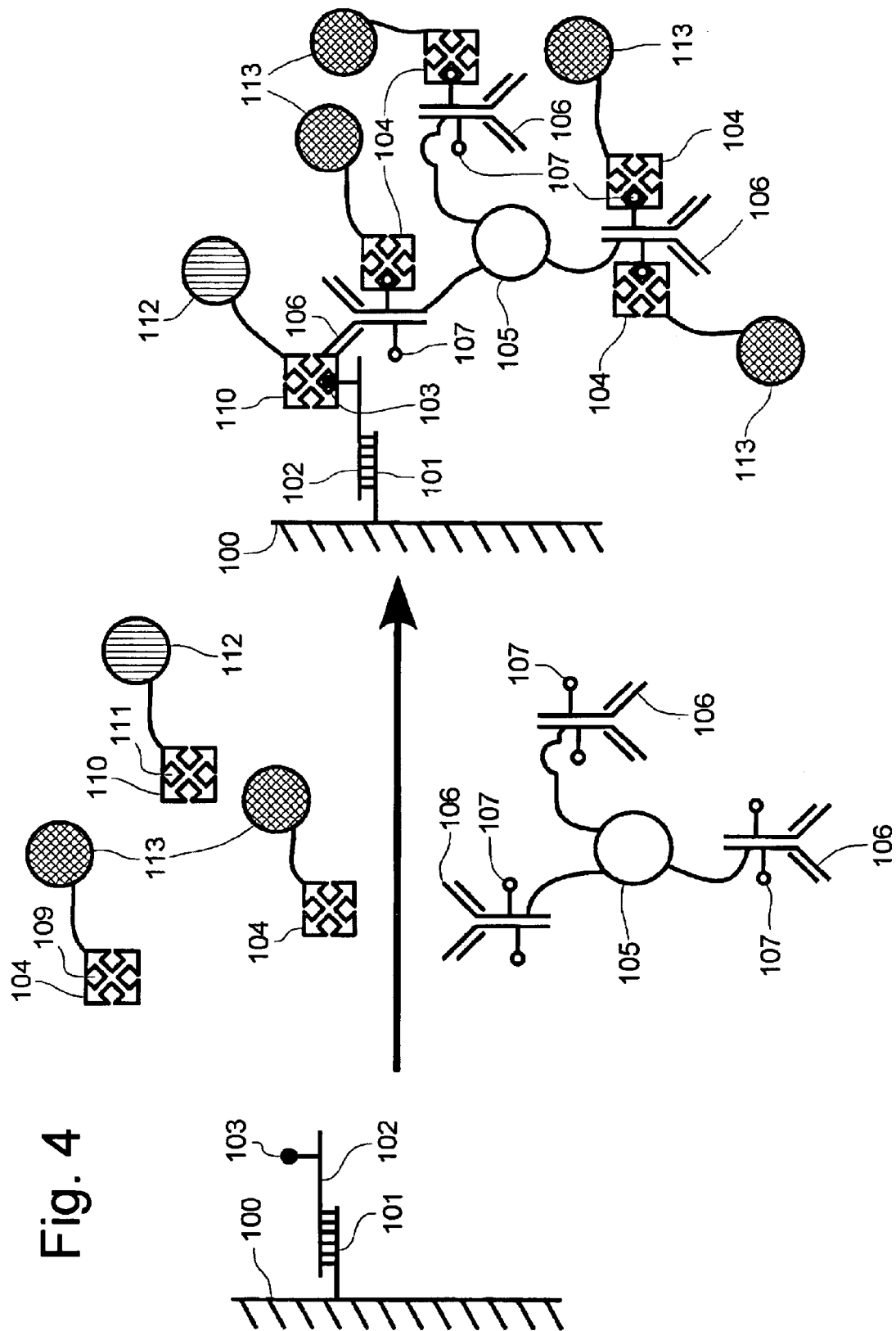
FIG. 4 is a schematic illustration of one embodiment of the presently claimed invention in which signal amplification is achieved by complexing a hybridized target molecule to a plurality of detectable moieties via a differentially detectable microparticle.

In some cases a signal may be difficult to detect due to a very small target population or other reasons including detector-based limitations such as photon limitations or background problems. In these cases it is often desirable to amplify the signal. In another embodiment, the presently claimed invention provides methods for amplifying the detectable signal. The method comprises hybridizing a target molecule to a probe wherein the target comprises a binding ligand. The hybridized target is contacted with a first receptor comprising multiple sites capable of binding the binding ligand to complex the receptor to the binding ligand, the first receptor may or may not be attached to a detectable moiety. The first receptor is contacted with a microparticle that is conjugated to a plurality of anti-receptors which themselves comprise a binding ligand. The microparticle may or may not be detectable. The anti-receptors are exposed to a second receptor that is conjugated to a detectable moiety. The first and second receptor may or may not be the same. FIGS. 2–4 illustrate various possible methods of this embodiment.

In FIG. 2, a probe 101 is immobilized to a solid substrate 100. A target molecule 102, comprising a first binding ligand 103 is hybridized to the probe 101. A first receptor 104 comprising multiple first binding sites 109 and a detectable moiety 108 is introduced along with a detectable microparticle 105 that is conjugated to a plurality of anti-receptors 106 that comprise multiple second binding ligands 107. The anti-receptors 106 are capable of complexing with the first receptor 104. Furthermore, the second binding ligands 107 are capable of complexing with the first receptor 104. Additionally, the microparticle 105 and the detectable moieties 108 are capable of being detected using the same detection mechanism. In preferred embodiments, this process is conducted in a multi-step fashion in which the first step comprises exposing the hybridized target molecule to the first receptors 104, the second step comprises exposing the complex from the first step to anti-receptors 106, and the third step comprises exposing the complex from the second step to additional first receptors 104. The resulting interactions produce a structure in which the immobilized probe 101 is hybridized to the target molecule 102 that comprises a first binding ligand 103. The first binding ligand 103 is complexed to a first receptor 104 comprising a detectable moiety 108. The first receptor 104 is complexed to the anti-receptor 106 via second binding ligands 107 or via a direct receptor-anti-receptor interaction. Furthermore, the second binding ligands 107 may or may not be identical to the first binding ligands 103. The microparticle 105 is conjugated to a plurality of anti-receptors 106, each anti-receptor 106 comprises a plurality of second binding ligands 107. The second binding ligands 107 are each complexed to a first receptor 104 comprising a detectable moiety 108, resulting in an amplified signal produced by both the microparticle 105 and the detectable moieties 108.

As a non-limiting example of the above embodiment, a DNA probe of known sequence may be immobilized to a glass substrate at a known location. A plurality of biotinylated nucleic acid sequences are exposed to the DNA probe. A nucleic acid target sequence comprising a portion that is complementary to the DNA probe will hybridize to the DNA probe. Non-hybridized sequences are removed. The hybridized target is then exposed to streptavidin-phycoerythrin (SAPE) and dyed microparticles conjugated with biotinylated anti-streptavidin antibody. The SAPE complexes with the biotin on the target. The biotinylated anti-streptavidin microparticles complex with the streptavidin from the SAPE. SAPE molecules are then added to complex directly with the anti-streptavadin molecules and/or with the biotin on the anti-streptavidin molecules. The result is that multiple fluorophore labels bound to the target molecule produce an amplified detectable signal. In this example, the dye and phycoerythrin emit a detectable signal at the same wavelength so that both the microparticle and the phycoerythrin molecules contribute to the signal strength.

In FIG. 3, a probe 101 is immobilized to a solid substrate 100. A target molecule 102, comprising a first binding ligand 103 is hybridized to the probe 101. A first receptor 104 comprising a detectable moiety 108 and multiple first binding sites 109 that are capable of interacting with second binding ligands and a second receptor 110 comprising multiple second binding sites 111 that are capable of interacting with a first binding ligand 103, are introduced. The anti-receptors 106 are capable of complexing with the second receptor 110. Furthermore, the second binding ligands 107 are capable of complexing with the first receptor 104 via first binding sites 109. Note that in this example, the microparticle 105 is not detectable. The resulting interactions produce a structure in which the immobilized nucleic acid probe 101 is hybridized to the target 102 that comprises a first binding ligand 103. The first binding ligand 103 is complexed to a second receptor 110 via a second binding site 111. The second receptor 110 is complexed to an anti-receptor 106 comprising second binding ligands 107 and a microparticle 105. The microparticle 105 is conjugated to a plurality of anti-receptors 106, each anti-receptor 106 comprising a plurality of second binding ligands 107. The second binding ligands 107 are each complexed to a first receptor 104 comprising a detectable moiety 108, resulting in an amplified signal produced by the binding moieties.

As a non-limiting example of the above embodiment, a DNA probe of known sequence may be immobilized to a glass substrate at a known location. A plurality of biotinylated nucleic acid sequences are then exposed to the DNA probe. A nucleic acid target sequence comprising a portion that is complementary to the DNA probe will hybridize to the DNA probe. Non-hybridized sequences are removed. The hybridized target is exposed to streptavidin (SA). Microparticles conjugated with biotinylated anti-streptavidin antibody are then added. The SA complexes with the biotin on the target. Anti-streptavidin microparticles are then added to complex with the SA. SAPE molecules are then introduced to complex with the biotin on the anti-streptavidin molecules. The result is multiple fluorophore labels bound to the target molecule producing an amplified signal. In this example, only the phycoerythrin added in the final labeling step produces the signal.

In FIG. 4, a probe 101 is immobilized to a solid substrate 100. A target molecule 102, comprising a first binding ligand 103 is hybridized to the probe 101. A first receptor 104 comprising a first detectable moiety 113 and multiple first binding sites 109 that are capable of interacting with a second binding ligand 107, a second receptor 110 comprising a second detectable moiety 112 and multiple binding sites 111 that are capable of interacting with a first binding ligand 103, and a detectable microparticle 105 that is conjugated to a plurality of anti-receptors 106 that comprise multiple second binding ligands 107, are introduced. First binding ligand 103 and second binding ligand 107 may or may not be identical. The anti-receptors 106 are capable of directly complexing with the first receptor 104, alternatively, the anti-receptors 106 are capable of interacting with the second receptor 110 via the second binding ligand 107. In this example, the first detectable moiety 113, the second detectable moiety 112 and detectable microparticle 105 are each detectable by a different mechanism. This enables the practitioner to study the assay by detecting each step individually. These components are all allowed to interact and the resulting interactions produce a structure in which the immobilized nucleic acid probe 101 is hybridized to the target molecule 102 that comprises a first binding ligand 103. The first binding ligand 103 is complexed to a second receptor 110, comprising second detectable moiety 112. The second receptor 110 is complexed to an anti-receptor 106 comprising second binding ligands 107 and a detectable microparticle 105. The microparticle 105 is conjugated to a plurality of anti-receptors 106, each anti-receptor 106 comprising a plurality of second binding ligands 107. The second binding ligands 107 are each complexed to a [second] first receptor 104 comprising a second detectable moiety 112, resulting in an amplified signal produced by the binding moieties and the ability to distinguish each binding interaction by utilizing various different detection methods.

As a non-limiting example of the above embodiment, a DNA probe of known sequence may be immobilized to a glass substrate at a known location. A plurality of biotinylated nucleic acid sequences are exposed to the DNA probe. A nucleic acid target sequence comprising a portion that is complementary to the DNA probe will hybridize to the DNA probe. Non-hybridized sequences are removed. The hybridized target is exposed to streptavidin-fluorescein (SAPE) and then to microparticles conjugated with biotinylated anti-streptavidin antibody. In this example, the microparticles are labeled with a label that is detectable at a different wavelength from the fluorescein. The SAFI complexes with the biotin on the target. The anti-streptavidin microparticles complex with the streptavidin from the SAFI SAPE molecules are then introduced and allowed to complex with the biotin on the anti-streptavidin molecules. The result is multiple fluorophore labels bound to the target molecule producing an amplified signal. In addition, because the SAFI, the labeled microparticle, and the phycoerythrin molecules are all independently detectable, each step of the assay can be monitored by scanning at different wavelengths corresponding to each type of detectable label.

In a further embodiment, the disclosed methods could be employed to differentially label different target molecules. By manipulating the ligand-receptor interactions, it is possible to label different target molecules in such a way that they can be differentially detected. This may involve using two different color labels or labels that are detectable at different wavelengths or any other known method of differential detection.

For example, a first target molecule comprising a first binding ligand is hybridized to a first immobilized probe. A second target molecule comprising a second binding ligand, is hybridized to a second immobilized probe. A first receptor comprising a first detectable moiety and multiple binding sites that are capable of interacting with the first binding ligand is introduced, forming a first complex. A second receptor comprising a second detectable moiety and multiple binding sites that are capable of interacting with the second binding ligand, is introduced forming a second complex. A first detectable microparticle that is conjugated to a plurality of first anti-receptors that comprise multiple binding ligands capable of binding the first receptors are introduced to complex with the first complex, thus forming a third complex. A second detectable microparticle that is conjugated to a plurality of second anti-receptors that comprise multiple binding ligands capable of binding the second receptors are introduced to complex with the second complex, thus forming a fourth complex. The first and second detectable moieties are differentiable from each other, as are the first and second detectable microparticles. The first detectable moiety and the first detectable microparticle, may or may not be differentially detectable. Likewise, the second detectable moiety and the second detectable microparticle may or may not be differentially detectable.

This embodiment may be employed in a variety of assays, including, for example, when it is desirable to differentially label targets from two different sample populations.

Spherical beads or particles have been commercially available as a tool for biochemists for many years. For example, antibodies conjugated to beads create relatively large particles specific for particular ligands. The large antibody-coated particles are routinely used to cross-link receptors on the surface of a cell for cellular activation, are bound to a solid phase for immunoaffinity purification, and may be used to deliver a therapeutic agent that is slowly released over time, using tissue or tumor-specific antibodies conjugated to the particles to target the agent to the desired site.

The most common method of covalently binding an antibody to a solid phase matrix is to derivatize a bead with a chemical conjugation agent and then bind the antibody to the activated bead. The use of a synthetic polymeric bead rather than a protein molecule allows the use of much harsher derivitization conditions than many proteins can sustain, is relatively inexpensive, and often yields a linkage that is stable to a wide range of denaturing conditions. A number of derivatized beads are commercially available, all with various constituents and sizes. Beads formed from synthetic polymers such as polyacrylamide, polyacrylate, polystyrene, or latex are commercially available from numerous sources such as Bio-Rad Laboratories (Richmond, Calif.) and LKB Produkter (Stockholm, Sweden). Beads formed from natural macromolecules and particles such as agarose, cross-linked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia. Magnetic beads are commercially available from sources such as Dynal Inc. (Great Neck, N.Y.).

Nucleic acid hybridization assay procedures and conditions developed in the art may be used, as described, for example in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983).

Nucleic acid hybridization buffers that may be used include phosphate and TRIS buffers, for example, at a pH of about 6 to 8. In one embodiment, a standard saline phosphate ethylenediaminetetraacetic acid ("SSPE") buffer is used. An exemplary phosphate buffer includes: 0.06M $H_2PO_4/HPO_4$, 1M Na$^+$, 0.006M EDTA (ethylenediaminetetraacetic acid), 0.005% of the generic product octylphenol ethylene oxide condensate, the generic form is also known as PEG (9–10) p-t-octylphenol, sold under TRITON X-100, as described by Sigma, at a pH of about 6.8, referred to herein as "6×SSPE-T". In one preferred embodiment, in a nucleic acid hybridization assay, a sulfonate hybridization buffer is used, for example a buffer including 2-[N-morpholino]ethanesulfonic acid ("MES"). For example, the hybridization buffer may include about 0.01 M to about 2 M MES or more, e.g., about 0.25 M MES, at a pH, for example, of about 6 to 7. In one embodiment, the MES buffer includes: 0.25 M MES, 1 M Na$^+$, and 0.005% of the generic product octylphenol ethylene oxide condensate sold under TRITON X-100, as described by Sigma, at a pH of about 6.7. The hybridization may be conducted, for example, at about 25 to 70° C., for example, about 45° C. Optionally, the buffer may be filtered prior to use, for example, through a 2 µm filter.

Examples of ligands and/or receptors include, but are not limited to, agonists and antagonists for cell membrane receptors, toxins and venoms, viral epitopes, hormones such as steroids, hormone receptors, peptides, enzymes and other catalytic polypeptides, enzyme substrates, cofactors, drugs including small organic molecule drugs, opiates, opiate receptors, lectins, sugars, saccharides including polysaccharides, proteins, and antibodies including monoclonal antibodies and synthetic antibody fragments, cells, cell membranes and moieties therein including cell membrane receptors, and organelles. Examples of ligand-receptor pairs include antibody-antigen; lectin-carbohydrate; peptide-cell membrane receptor; protein A-antibody; hapten-antihapten; digoxigenin-anti-digoxigenin; enzyme-cofactor and enzyme-substrate.

Preferably, a ligand-receptor pair includes a receptor that is capable of binding a plurality, e.g., 2, 3, 4 or more, molecules of the ligand. In one preferred embodiment, the ligand-receptor pair is biotin-avidin or biotin-streptavidin. The vitamin biotin is detected by binding of the indicator protein avidin, isolated from egg white, or streptavidin, isolated from *Streptomyces avidinii* bacteria. Avidin and streptavidin have four high affinity binding sites for biotin with a binding constant of about K=10$^{15}$ mol$^{-1}$. Kessler, *Overview of Nonradioactive Labeling Systems* in "Nonradioactive Labeling and Detection of Biomolecules", C. Kessler, Ed., Springer-Verlag, New York, 1992, pp. 27–34, the disclosure of which is incorporated herein.

In one embodiment of the presently claimed invention, the binding ligand is biotin and the receptors may be avidin, streptavidin, streptavidin phycoerythrin (SAPE), streptavadin fluorescein (SAFI), neutralite™-avidin, any derivative of strepavidin, or any other molecule capable of binding biotin.

The methods disclosed herein can utilize any of a variety of members of ligand receptor binding pairs available in the art. In one preferred embodiment, in nucleic acid hybridization assays using an immobilized probe nucleic acid capable of hybridizing to a target nucleic acid, the target nucleic acid is attached to a binding ligand constituting a member of a ligand-receptor binding pair. Additionally, the microparticle includes a plurality of the binding ligands. Preferably, the receptor of the ligand receptor pair is capable of binding to two or more molecules of ligand. For example the ligand may be biotin, and the receptor may be avidin or streptavidin, each of which are capable of binding four molecules of biotin.

Methods available in the art for attaching binding molecules to nucleic acids may be used to attach ligands or receptors to nucleic acid targets. In one embodiment, nucleic acids having a binding molecule covalently attached by can be synthesized using a DNA synthesizer and standard phosphoramidite reagents. For example, biotin phosphoramidites for direct labeling of synthetic oligonucleotides may be used. Biotin phosphoramidites are commercially available from Glen Research Corporation, Sterling, Va.

In one embodiment, in the case where the binding ligand is biotin, biotinylated DNA targets can be prepared using nick translation and random primer extension, while biotinylated RNA targets can be synthesized by in vitro transcription using an RNA polymerase. Biotinylated deoxyribonucleoside triphosphates and ribonucleoside triphosphates have been used for the enzymatic preparation of biotinylated DNA and biotinylated RNA. Exemplary methods are disclosed in detail in Rashtchian and Mackey, *Labeling and Detection of Nucleic Acids,* in "Nonradioactive Labeling and Detection of Biomolecules", C. Kessler, Ed., Springer-Verlag, New York, 1992, pp. 70–84. The concentration of biotin molecules may be increased by the use of a psoralen biotin reagent, as described in Levenson et al., *Methods Enzymol,* 184:577–583 (1990); and Cimono et al., *Ann. Rev. Biochem.* 54:1151–1193 (1985), the disclosures of each of which are incorporated herein. Background hybridization may be reduced by HPLC purification of biotinylated target nucleic acids.

Methods available in the art for attaching binding molecules to solid surfaces may be used to attach ligands or receptors to microparticles.

Biotinylated antibodies, such as biotinylated anti-streptavidin molecules, are available commercially, for example, from Vector Laboratories (Burlingame, Calif.).

Hybridization of the target molecule to the probe is detected by detecting the presence of a complexed microparticle. The microparticle is detected, e.g., by providing a label on the microparticle, or by detecting the presence of detectable moieties that are complexed to the microparticle via a receptor-anti-receptor interaction.

A variety of labels may be used in the assay methods disclosed herein. The label may be provided on the amplification reagent, the receptor and/or the binding ligand. Examples of labels include fluorescent labels, chemiluminescent labels, and inorganic labels, such as gold, as well as enzymatic labels.

Labels may be used that are detectable, for example, by chromogenic detection, chemiluminescent detection and fluorescent detection. Labels that may be used include marker enzymes such as alkaline phosphatase ("AP"), ∃-galactosidase or horseradish peroxidase, which are detected using a chromogenic substrate. For example, AP may be detected using 5-bromo-4-chloro-3-indolyl phosphate or nitroblue tetrazolium salt.

Other labels include fluorescent tags such as fluorescein, rhodamine, and resorufin, and derivatives thereof, as well as coumarins such as hydroxycoumarin. Additionally fluorescence resonance energy transfer may be measured, as described in Cardullo, *Nonradiative Fluorescence Resonance Energy Transfer* in "Nonradioactive Labeling and Detection of Biomolecules", C. Kessler, Ed., Springer-Verlag, New York, 1992, pp. 414–423, the disclosure of which is incorporated herein. Optionally inorganic labels may be used, such as colloidal gold particles or ferritin. The use of colloidal gold particles as labels is described, for example, in Van de Plas and Leunissen, *Colloidal Gold as a Marker in Molecular Biology: The Use of Ultra-Small Gold Particles,* in "Nonradioactive Labeling and Detection of Biomolecules", C. Kessler, Ed., Springer-Verlag, New York, 1992, pp. 116–126, the disclosure of which is incorporated herein.

Reagents for labeling streptavidin or avidin with a fluorescent tag are commercially available. For example, the reagents, 5(6)-Carboxyfluorescein-N-hydroxysuccinimide ester (FLUOS), 7-amino-4-methyl-counarin-3-acetic acid-N'-hydroxysuccinimide ester (AMCA, acitvated) and fluorescein isothiocyanate (FITC) are available from Boehringer Mannheim, Indianapolis, Ind. Methods for fluorescently labeling proteins with fluorescent labels, and methods for detection of the fluorescent labels, are described in Howard, G., *Labeling Proteins with Fluorochromes*, in "Methods in Nonradioactive Detection," G. Howard, Ed., Appleton and Lange, Norwalk, Conn., 1993, pp. 39–68, the disclosure of which is incorporated herein. Additionally, there are a variety of commercially available labeled streptavidin and avidin molecules. Examples include streptavidin-gold, streptavidin-fluorochrome, streptavidin-AMCA, streptavidin-fluorescein, streptavidin-phycoerythrin (SAPE), streptavidin-sulforhodamine 101, avidin-FITC and avidin-Texas red®, which are commercially available from Boehringer Mannheim, Indianapolis, Ind.

Methods of making fluorescent microparticles are described, for example, in U.S. Pat. Nos. 5,132,242 and 5,194,300.

In another embodiment, an array comprising a plurality of different nucleic acid probes immobilized on a surface, each having a defined sequence and location on the surface, may be used in the assays disclosed herein, thus permitting screening and detection of binding of a large number of nucleic acids in a sample.

Methods for conducting nucleic acid hybridization assays have been well developed in the art. Hybridization assay procedures and conditions will vary depending on the application and are selected in accordance with the general binding methods known including those referred to in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983), each of which are incorporated herein by reference.

Methods for screening using arrays of polymers, such as nucleic acids, immobilized on a solid substrate, are disclosed, for example, in U.S. Pat. No. 5,510,270, the disclosure of which is incorporated herein. In this method, an array of diverse nucleic acids is formed on a substrate. The fabrication of arrays of polymers, such as nucleic acids, on a solid substrate, and methods of use of the arrays in different assays, are described in: U.S. Pat. Nos. 5,143,854, 5,242,979, 5,252,743, 5,324,663, 5,384,261, 5,405,783, 5,412,087, 5,424,186, 5,445,934, 5,451,683, 5,482,867,5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, 5,856,011, 5,858,695, 5,861,242, 5,871,928, 5,874,219, 5,858,837, 5,919523, 5,925,525, 5,959,098, 5,968,740, 5,981,185, 6,013,440, 6,022,963, 6,027,880, 6,040,138, 6,045,996, and 6,083,697 all of which are incorporated by reference in their entirety for all purposes. Accessing genetic information using high density DNA arrays is further described in Chee, *Science* 274:610–614 (1996), the disclosure of which is incorporated herein by reference. The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS®). U.S. Pat. No. 5,631,734, the disclosure of which is incorporated herein.

Substrates having a surface to which arrays of polynucleotides are attached are referred to herein as "biological chips". The substrate may be, for example, silicon or glass, and can have the thickness of a microscope slide or glass cover slip. Substrates that are transparent to light are useful when the assay involves optical detection, as described, e.g., in U.S. Pat. No. 5,545,531, the disclosure of which is incorporated herein. Other substrates include Langmuir Blodgett film, germanium, (poly)tetrafluorethylene, polystyrene, gallium arsenide, gallium phosphide, silicon oxide, silicon nitride, and combinations thereof.

In the embodiment wherein arrays of nucleic acids are immobilized on a surface, the number of nucleic acid sequences may be selected for different applications, and may be, for example, about 100 or more, or, e.g., in some embodiments, more than $10^5$ or $10^8$. In one embodiment, the surface comprises at least 100 probe nucleic acids each preferably having a different sequence, each probe contained in an area of less than about 0.1 $cm^2$, or, for example, between about 1 $cm^2$ and 10,000 $cm^2$, and each probe nucleic acid having a defined sequence and location on the surface. In one embodiment, at least 1,000 different nucleic acids are provided on the surface, wherein each nucleic acid is contained within an area less than about $10^{-3}$ $cm^2$, as described, for example, in U.S. Pat. No. 5,510,270.

Arrays of nucleic acids for use in gene expression monitoring and genotyping are described in PCT WO 98/15151, and U.S. Pat. Nos. 6,040,138, 6,033,860, 5,871,928, 5,800,992, 6,027,880, 6,027,894, 5,968,740, 5,925,525, 5,858,659, 5,710,000, 5,974,164, 5,856,104 and 5,795,716 each of which is hereby incorporated by reference for all purposes. In one embodiment, arrays of nucleic acid probes are immobilized on a surface, wherein the array comprises more than 100 different nucleic acids and wherein each different nucleic acid is localized in a predetermined area of the surface, and the density of the different oligonucleotides is greater than about 60 different oligonucleotides per 1 $cm^2$.

Arrays of nucleic acids immobilized on a surface that may be used also are described in detail in U.S. Pat. No. 5,744,305, the disclosure of which is incorporated herein. As disclosed therein, on a substrate, nucleic acids with different sequences are immobilized each in a predefined area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 $cm^2$ to $10^{-10}$ $cm^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-10}$ $cm^2$. For example, in one embodiment, there is provided a planar, non-porous support having at least a first surface, and a plurality of different nucleic acids attached to the first surface at a density exceeding about 400 different nucleic acids/$cm^2$, wherein each of the different nucleic acids is attached to the surface of the solid support in a different predefined region, has a different determinable sequence, and is, for example, at least 4 nucleotides in length. The nucleic acids may be, for example, about 4 to 20 nucleotides in length. The number of different nucleic acids may be, for example, 1000 or more.

In one embodiment, fused silica substrates may be used which have a low glass fluorescence background. Silica substrates permit a low exposure print gap with little or no signal falloff in going from 50 cm to 20 cm features, and yields improved performance, including signal and discrimination, for feature sizes less than 50:m, for example, 2:m. A description of solid phase chemistry, photolithography, and data collecting methods, for the synthesis and use of arrays of materials attached to a solid substrate is provided in U.S. Pat. No. 5,744,305, the disclosure of which is incorporated herein.

In the embodiment wherein solid phase chemistry, photolabile protecting groups and photolithography are used to create light directed spatially addressable parallel chemical synthesis of a large array of polynucleotides on the substrate, as described in U.S. Pat. No. 5,527,681, the disclosure of which is incorporated herein, computer tools may be used for forming arrays. For example, a computer system may be used to select nucleic acid or other polymer probes on the substrate, and design the layout of the array as described in U.S. Pat. No. 5,571,639, the disclosure of which is incorporated herein.

In the embodiment where polynucleotides of a known chemical sequence are synthesized at known locations on a substrate, and hybridization of a nucleic acid is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270, the disclosure of which is incorporated herein.

Devices for concurrently processing multiple biological chip assays may be used as described in U.S. Pat. No. 5,545,531, the disclosure of which is incorporated herein. Methods and systems for detecting a labeled marker on a sample on a solid support, wherein the labeled material emits radiation at a wavelength that is different from the excitation wavelength, radiation is collected by collection optics and imaged onto a detector that generates an image of the sample, are disclosed in U.S. Pat. No. 5,578,832, the disclosure of which is incorporated herein. These methods permit a highly sensitive and resolved image to be obtained at high speed. Methods and apparatus for detection of fluorescently labeled materials are further described in U.S. Pat. Nos. 5,631,734 and 5,324,633, the disclosures of which are incorporated herein.

Methods of Use

The assay methods and compositions described herein may be used in a range of applications including biomedical and genetic research and clinical diagnostics. Arrays of polymers such as nucleic acids may be screened for specific binding to a target, such as a complementary nucleotide, for example, in screening studies for determination of binding affinity and in diagnostic assays. The nucleic acid arrays may be used in many applications including gene expression monitoring and detection of genetic diseases such as cystic fibrosis, diabetes, and acquired diseases 30 such as cancer, as disclosed in U.S. Pat. Nos. 5,861,242, 6,027,880 and 5,837,832, the disclosures of which are incorporated herein.

Gene expression may be monitored by hybridization of large numbers of mRNAs in parallel using high density arrays of nucleic acids in cells, such as in microorganisms such as yeast, as described in Lockhart et al., Nature Biotechnology, 14:1675–1680 (1996), the disclosure of which is incorporated herein. Bacterial transcript imaging by hybridization of total RNA to nucleic acid arrays may be conducted as described in Saizieu et al., Nature Biotechnology, 16:45–48 (1998), the disclosure of which is incorporated herein.

Other applications include chip based genotyping, species identification and phenotypic characterization, as described in U.S. Pat. No. 6,228,575, the disclosure of which is hereby incorporated by reference for all purposes.

In another embodiment, kits are provided for carrying out amplified nucleic acid hybridization assays that include in packaged combination the materials: immobilized probe nucleic acids, amplification reagents, and labeled receptors. These reagents will be, for example, in separate containers in the kit. The kit may also include hybridization buffers, wash solutions, negative and positive controls and written instructions for carrying out the assay.

All publications referred to herein are incorporated herein by reference in their entirety.

While nucleic acid targets and probes are discussed in detail herein by way of example, the methods and compounds disclosed herein may be used to detect the binding of other molecules including polypeptides. The invention will be further understood by the following non-limiting examples.

EXAMPLES

A schematic of the current Affymetrix GeneChip® Expression Array signal amplification assay is shown below. Signal amplification over the signal obtained with the first streptavidin-phycoerythrin (SAPE) stain is achieved via a biotinylated anti-streptavidin antibody (b-Ab) that can complex with the SAPE from the first stain. The antibody contains multiple sites where multiple SAPE molecules can bind in the $3^{rd}$ staining step.

Affymetrix GeneChip® Expression Array signal amplification:

probe:target-biotin==SAPE==biotinylated anti-streptavidin antibody (b-Ab)==SAPE step 1 —complex biotinylated target:probe duplex with streptavidin-phycoerythrin (SAPE)

step 2 —complex biotinylated anti-streptavidin antibody to complex in step 1 step 3 —complex multiple SAPE to complex in step 2

Microsphere particles were designed to be conjugated with the biotinylated anti-streptavidin antibody used in the current Affymetrix GeneChip® Expression Array signal amplification assay. The antibody-coated microsphere will replace the b-Ab as the reagent in the second step of the assay. The microsphere, with its large surface area, contains many biotinylated anti-streptavidin antibody molecules (b-Ab) that can bind streptavidin-phycoerythrin (SAPE) in the final labeling step of the assay. Compared with the current Affymetrix GeneChip® Expression Array signal amplification assay, which uses a single b-Ab molecule, the signal amplification should be greatly enhanced.

Figure 5:
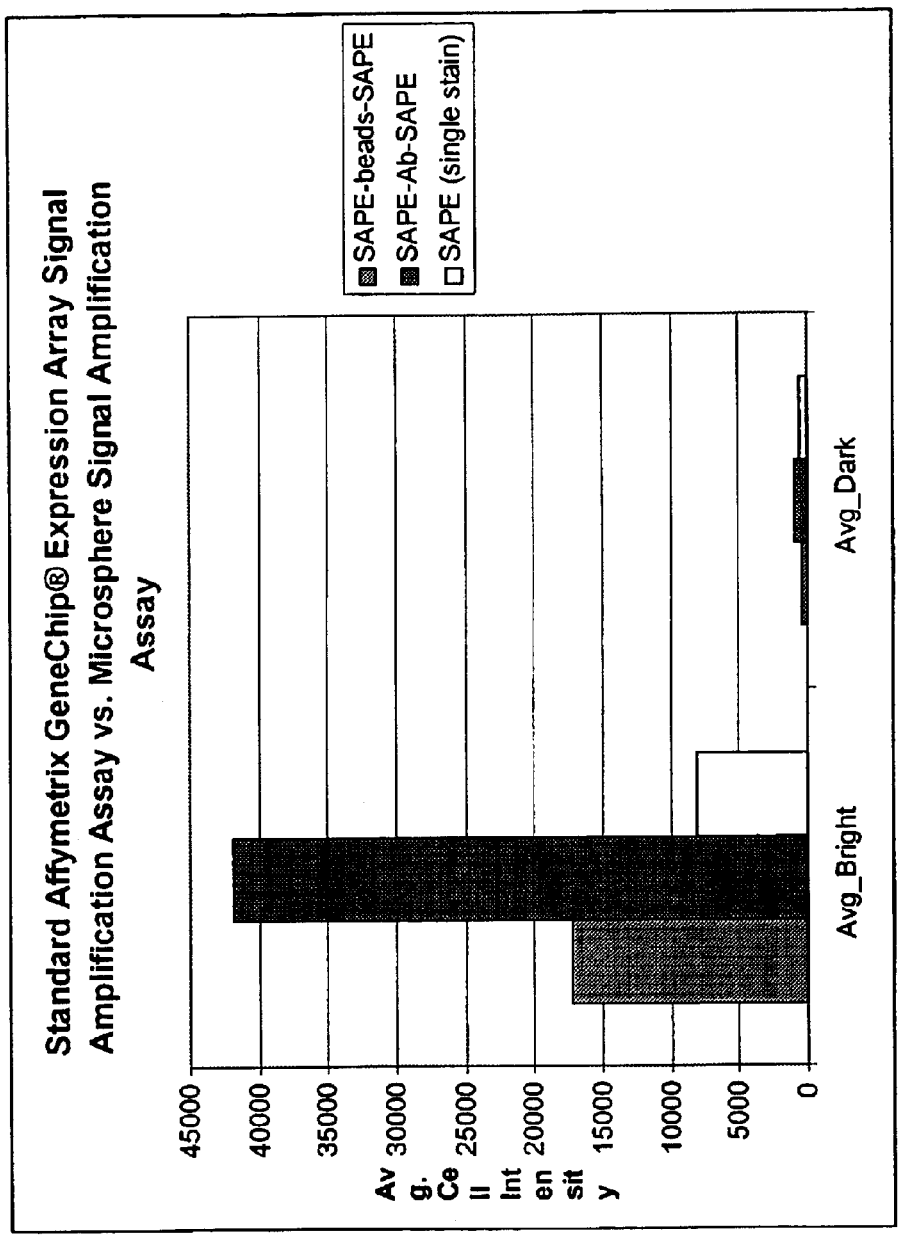
FIG. 5 depicts the results of an experiment using the microparticle labeling methods of the presently claimed invention.

Experiment 1 was designed to measure the signal amplification of the antibody-coated microspheres when used as a replacement for the b-Ab in the current Affymetrix GeneChip® Expression Array signal amplification assay. One experimental and two control assay conditions were tested: 1) the current Affymetrix GeneChip® Expression Array signal amplification assay using the microspheres in place of the b-Ab in step two, 2) the current Affymetrix GeneChips® Expression Array signal amplification assay, and 3) the current Affymetrix GeneChip® Expression Array single stain assay, which is identical to the signal amplification assay except for the omission of steps 2 and 3. Results from the study are shown in FIG. 5.

Amplication was approximately 2.5 fold over the single stain SAPE labeling with essential no non-specific binding due to the microspheres, as demonstrated by the comparably low signal levels in the background "dark" regions on the array.

What is claimed is:

1. A method for detecting a target, the method comprising:
   providing a substrate including a surface containing a plurality of nucleic acid probes;
   hybridizing a target with at least one probe, said target having a binding ligand;
   forming a detectable complex by contacting said hybridized target with a first receptor for said binding ligand, wherein said receptor is optionally part of a first complex, and a second-complex including a detectable microparticle, a plurality of anti-receptors that bind to said first receptor and a plurality of said binding ligand;
   removing unbound complexes; and
   detesting the microparticle.

2. The method of claim 1 wherein said binding ligand is biotin, said first receptor is streptavidin and said anti-receptor is a biotinylated anti-streptavidin antibody.

3. The method of claim 1 wherein said first receptor for said binding ligand is added as a first complex and wherein said first complex further comprises a detectable moiety and said detectable moiety is detected.

4. The method of claim 3 wherein said detectable microparticle and said detectable moiety are differentially detectable.

5. A method for detecting a target, the method comprising:
   providing a substrate including a surface containing a plurality of nucleic acid probes;
   hybridizing a target with at least one probe, said target having a first binding ligand; and
   contacting said hybridized target with:
   a first complex including a receptor for said first binding ligand and optionally a first detectable moiety;
   a second complex including a detectable microparticle, an anti-receptor for said first receptor complex and a second binding ligand; and
   a third complex including a receptor for said second binding ligand and optionally a second detectable moiety;
   removing unbound complexes; and
   detecting the presence of the microparticle.

6. The method of claim 5 wherein said fist detectable moiety is detected.

7. The method of claim 6 wherein said microparticle and said first detectable moiety are differentially detectable.

8. The method of claim 5 wherein said second detectable moiety is detected.

9. The method of claim 8 wherein said microparticle and said second detectable moiety are differentially detectable.

* * * * *